United States Patent [19]

Boegershausen et al.

[11] Patent Number: 4,721,917

[45] Date of Patent: Jan. 26, 1988

[54] COATING CONTINUITY DETECTOR

[75] Inventors: Robert L. Boegershausen, Chesterfield County; Joachim W. Illig, deceased, late of Henrico County, both of Va., by Ann G. Illig, administrator

[73] Assignee: Reynolds Metals Company, Richmond, Va.

[21] Appl. No.: 843,856

[22] Filed: Mar. 21, 1986

Related U.S. Application Data

[63] Continuation of Ser. No. 660,293, Oct. 12, 1984.

[51] Int. Cl.⁴ .................... G01R 31/12; G01R 31/08
[52] U.S. Cl. .................... 324/558; 324/513; 209/572
[58] Field of Search .................. 324/558, 513, 515; 209/572

[56] References Cited

U.S. PATENT DOCUMENTS

| | | |
|---|---|---|
| 1,717,193 | 6/1929 | Dantsizen . |
| 1,827,349 | 10/1931 | Bing . |
| 2,141,052 | 12/1938 | Stephano . |
| 2,506,454 | 5/1950 | Holmwood . |
| 2,890,409 | 6/1959 | Krevelen .................... 324/558 |
| 2,894,204 | 7/1959 | Gambrill .................... 324/54 |
| 2,941,144 | 6/1960 | Cannon . |
| 2,978,636 | 4/1961 | Fountain .................... 324/54 |
| 3,247,454 | 4/1966 | Gale .................... 324/558 |
| 3,343,081 | 9/1967 | Lane .................... 324/54 |
| 3,413,541 | 11/1968 | Swim et al. . |
| 3,465,242 | 9/1969 | Gruetzmacher .................... 324/558 |
| 3,541,437 | 11/1970 | Ahrweiler . |
| 3,636,442 | 1/1972 | Doi . |
| 3,710,241 | 1/1973 | Dineen .................... 324/558 |
| 3,792,458 | 2/1974 | Smith .................... 324/558 |
| 3,970,924 | 7/1976 | Pendleton .................... 324/54 |
| 4,446,422 | 5/1984 | Koehler .................... 324/54 |

Primary Examiner—Reinhard J. Eisenzopf
Assistant Examiner—Jose M. Solis
Attorney, Agent, or Firm—Alan T. McDonald

[57] ABSTRACT

A method and apparatus are disclosed for detecting the continuity of nonconductive coatings on conductive web materials, such as rolls of metallic foils. The coated side of the sheet material web contacts a conductive surface and electrical resistance of the coating is measured. The apparatus for measuring the resistance of the coating may be adjusted to permit small gaps in the coating to be bypassed while being triggered by major gaps in the coating.

23 Claims, 2 Drawing Figures

COATING CONTINUITY DETECTOR

This application is a continuation of application Ser. No. 660,293, filed Oct. 12, 1984.

BACKGROUND OF THE INVENTION

Metallic foils, such as aluminum foil, tin foil and the like, are useful materials in forming laminated structures. These materials may add strength to such laminates, act as light and/or vapor barriers, or merely act to give a "quality look" to packaging materials.

When forming laminated structures which include one or more metallic foil layers, it is often necessary to coat or prime the metallic foil prior to lamination. This is true, for example, when bonding aluminum foil to plastics resin film layers, such as polypropylene. Such coatings as epoxys, vinyls, polypropylene dispersions, nitrocellulose, ethyl cellulose and others are thus routinely applied to metallic foils.

During production, these coatings are applied to the metallic foils by unwinding the foil in web form from a roll, coating the foil, drying and/or curing the coating and rewinding the foil onto another roll. At production speeds, no mechanical device has been heretofore known which was capable of detecting gaps in the coating on the metallic foil over a substantial length of the foil. Thus, these gaps were detected visually by an operator of the coating apparatus as the coated foil passed his operating station.

The accuracy of such manual coating continuity detection is limited for several reasons. First, many of the coatings placed on metallic foils are transparent or nearly transparent. Thus, accurate visual inspection is highly difficult. Even when applying coatings that are relatively easy to inspect, distractions of the operator, and the sheer boredom of continuously watching coated foil pass the operator station, can lead to the failure of the operator to detect a substantial coating gap.

It is desirable, therefore, to provide a method and apparatus for mechanically detecting the continuity of coatings on metallic foils which is free from operator judgment.

While major gaps in such coatings cannot be tolerated, complete coverage of even thickness on the foil of the coating material is not always completely necessary in commercial practice. Thus, minor pinholes or thickness variations in the coating may often be tolerated. It is also desirable, therefore, that a mechanized coating continuity detection method and apparatus be capable of differentiating major gaps in the coating requiring corrective attention from minor acceptable gaps, such as pinholes, minor thickness variations and the like, which are not a cause for concern.

THE PRESENT INVENTION

By means of the present invention, these desired results are obtained. The method and apparatus of the present invention comprises electrically grounding a conductive sheet material web, such as a metallic foil, prior to coating thereof, applying a nonconductive coating to the sheet material web, contacting the coated side of the web with a conductive surface which is electrically insulated and detecting electrical resistance between the web and the detection surface caused by the coating material. The detection means may be connected to an alarm system, or may be connected to deactivate the coating operation or mark the web at the defect when a gap in the coating is detected. The detection apparatus also is adjustable to respond only to continuous gaps in the coating of a time sufficient in relation to the speed of the web past the detecting means corresponding to gaps of a size warranting corrective action.

BRIEF DESCRIPTION OF THE DRAWINGS

The coating continuity detection method and apparatus of the present invention will be more fully described with reference to the drawings in which.

DETAILED DESCRIPTION OF THE PREFERRED EMBODIMENT

Figure 1:
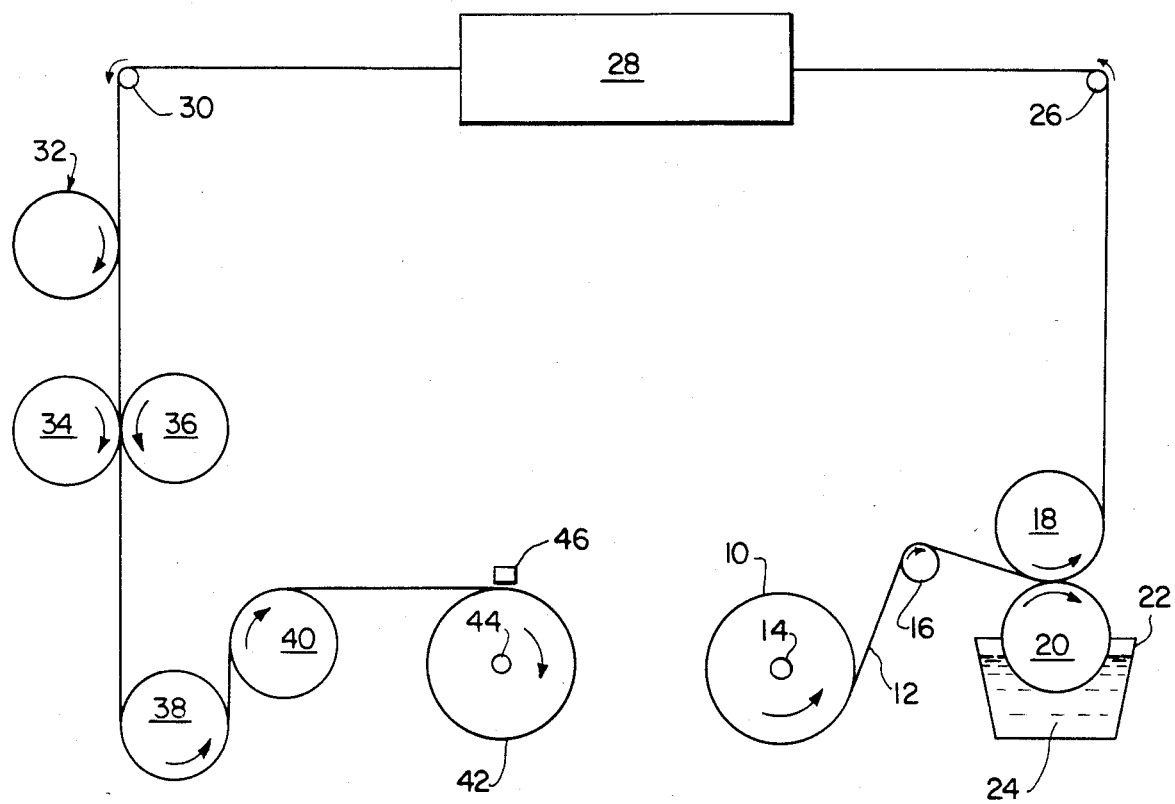
FIG. 1 is a schematic representation of a conductive web coating line, including the coating continuity detection system of the present invention.

Turning to the FIGURES, a web 12 of a conductive sheet material, such as a metallic foil, including aluminum foil, tin foil and the like, or a laminate including a metallic foil surface, is supplied from a roll 10 of the sheet material carried upon reel 14. As the web 12 leaves the roll 10, it passes over a guide roll 16. The guide roll 16, besides performing its guide function, may be electrically grounded, thus electrically grounding the conductive web 12 prior to coating, for reasons which will be explained below. Alternatively, the frame (not shown) carrying roll 14 and web 12 may be electrically grounded to provide the grounding function for web 12.

After leaving the guide roll 16, the web 12 passes through the nip between a pair rollers 18 and 20. Rollers 18 and 20 may be driven rollers, to supply driving force to the web 12. However, these rollers 18 and 20 may also be free-wheeling rollers with the driving force for the web 12 being supplied by a takeup reel 44. Typically, roller 20 is a gravure roll, however, roll 20 may have a smooth surface. Roll 18 is typically a rubber roll.

Roller 20 is partially submerged within a tank 22 containing coating material 24. This coating material is of a nonconductive nature, and may be formed from materials such as epoxies, vinyls, polypropylene dispersions, nitrocellulose, ethyl cellulose, and other similar nonconductive coatings routinely applied to conductive webs, such as metallic foils. As the web 12 passes between rollers 18 and 20, the surface of the web 12 contacting roller 20 is thus coated with the coating material 24.

The web 12 leaves rollers 18 and 20 and passes over a free-wheeling guide roller 26 and into an oven 28. Within the oven 28, the coating material 24 is dried and/or cured, depending upon the nature of the coating material 24. For some coatings, oven 28 is not required, with air drying of the coating material 24 being sufficient.

The web 12 next passes over another free-wheeling guide roller 30 and contacts coating continuity detection means generally shown at 32, the operation of which will be more fully described below. Web 12 may next pass between an optional additional pair of rollers 34 and 36, over free-wheeling guide rollers 38 and 40 and finally onto a take-up roll 42 mounted upon the driven reel 44.

As previously mentioned, the driving force for the web 12 could be supplied entirely by reel 44. In that case, rollers 16, 18, 20, 26, 30, 34, 36, 38 and 40 will all be free-wheeling rollers. If, however, driving force for the web 12 along its path is desired, driven roller pairs 18 and 20 and 34 and 36 operate at the same speed as take-up reel 44, to maintain uniform tension in the web 12 throughout its travel.

Figure 2:
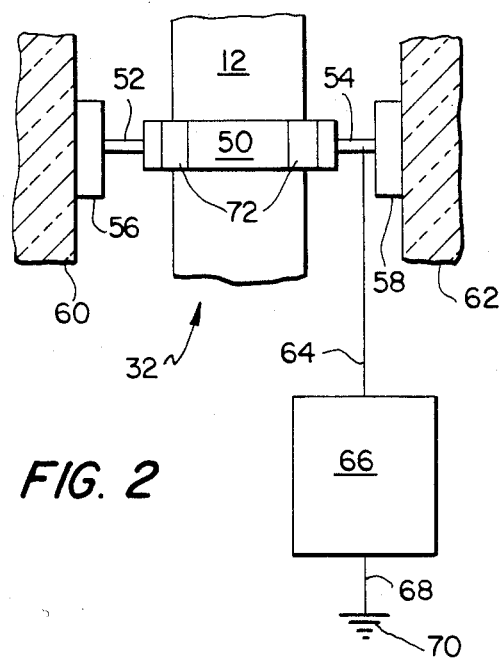
FIG. 2 is a front elevational view of the coating continuity detection apparatus.

Looking now more closely at the coating continuity detector 32, its operation is more fully illustrated in FIG. 2.

As the web 12 passes from guide roll 30, it contacts a free-wheeling roll 50. Roll 50 is formed of a conductive material, such as stainless steel, or aluminum, and is free-wheeling upon its supporting shaft members 52 and 54. Preferably, this roll 50 is covered with a conductive polymer coating. This serves to protect roll 50 from corrosion, is easily cleaned and provides a practical and convenient way of passing electrical current without excessive sensitivity. Roll 50 is electrically connected through line 64 to a coating continuity detection apparatus 66. Detection apparatus 66 is electrically grounded to ground 70 through line 68. As previously mentioned, web 12 was electrically grounded at roll 16, and since all eleccrtrical grounds are common, a completed circuit has thus been formed. In order to maintain this circuit, insulators 56 and 58 electrically isolate roll 50 from an electrical ground, such as the frame members 60 and 62 upon which roll 50 is mounted.

When applying an extremely low voltage, said voltage being in the range of about 1.15 to about 11.5 volts DC, to prevent sparking, to the electrical circuit formed, the non-conductive coating material 24 causes electrical resistance to occur between the conductive web 12 and roll 50. The detection apparatus 66 senses this resistance. Should a gap occur in the coating upon web 12, the electrical resistance in the circuit falls significantly, and may fall practically to zero, and a reduction in or lack of voltage resulting therefrom is sensed by the detecting apparatus 66. This gap detection causes detection apparatus to signal the operator that a gap has occurred, to shut down the coating line for corrective action, or to mark the web 12 at the location of the defect. Such marking may be accomplished by marking means 46, which may be an ink jet marker, tape marker or the like and is timed to mark web 12 when the defect seen at detector 32 reaches roll 44.

As previously mentioned, not all gaps in the coating of web 12 are causes for alarm. Small pinholes and the like are acceptable in many instances. Yet, any gap in the nonconductive coating upon web 12 could produce a reduced or near zero voltage reading. Thus, detection apparatus 66 may include a timing means which is adjustable, based upon the speed of the line and the minimum size gap to be measured, to vary the sensitivity of the apparatus 66 such that only gaps of a minimum time span will trigger the alarm or shutdown mechanism. Thus, the detection apparatus 66 may be fine tuned to the specific coating operation taking place. Variations of the level of applied DC voltage may also help provide the fine tuning of the sensitivity of apparatus 66 necessary. These sensitivity controls may be used separately or in conjunction.

Looking again at roll 50, collars 72 are illustrated adjacent the side edges of web 12. Should there be a region along web 12, such as its side edges, where coating either does not take place or where the continuity of the coating is not significant, collars or masks 72 are positioned upon conductive roll 50 at the corresponding locations around roll 50 where these coating discontinuities in web 12 are permitted to occur. The collars 72 are of a nonconductive material, and thus will operate to cause resistance between web 12 and roll 50 in the same manner as if the coating material were in place. The collars 72 may be plastic collars, or may be any other non-conductive shielding material, including such nonconductive tapes as teflon tape, masking tape and the like.

From the foregoing, it is clear that the present invention provides an automated method and apparatus for determining the continuity of coatings upon conductive webs which permits such detection to be accomplished without operator intervention.

While presently preferred embodiments of the invention have been illustrated and described, it is clear that the invention may be otherwise variously praticed and embodied, within the scope of the following claims.

It is claimed:

1. A method for determining the continuity of a nonconductive coating material on a conductive material web comprising electrically grounding said web, electrically grounding a means for measuring electrical resistance, forming an electrical circuit by passing the coated side of said web against an ungrounded conductive surface and electrically connecting said means for measuring electrical resistance to said ungrounded conductive surface, masking a portion of said ungrounded conductive surface to permit a region of coating discontinuity on said web to pass thereacross without detection, applying electrical voltage through said electrical circuit and measuring the electrical resistance in said circuit.

2. The method of claim 1 wherein said measuring is varied in sensitivity.

3. The method of claim 2 wherein said varying of sensitivity comprises timing a length of reduced electrical resistance in said circuit.

4. The method of claim 2 wherein said varying of said sensitivity comprises varying said voltage applied to said circuit.

5. The method of claim 4 wherein said voltage is varied between about 1.15 and 11.5 volts.

6. The method of claim 4. wherein said varying of sensitivity further comprises timing a length of reduced electrical resistance in said circuit.

7. The method of claim 1 further comprising activating an alarm in response to a determination of a coating discontinuity.

8. The method of claim 1 further comprising ceasing coating of said nonconductive material onto said conductive material web in response to a determination of a coating discontinuity.

9. The method of claim 1 further comprising marking said web in response to a determination of a coating discontinuity.

10. Apparatus for determining the continuity of a nonconductive coating material on a conductive material web comprising means for electrically grounding said web, an ungrounded conductive surface, grounded means for measuring electrical resistance, means for electrically connecting said grounded means for measuring electrical resistance to said ungrounded conductive surface, means for passing the coated side of said web against said ungrounded conductive surface to complete an electrical circuit, masking means on said ungrounded conductive surface for permitting a region of coating discontinuity to pass thereacross without detection and means for applying an electrical voltage through said electrical circuit.

11. The apparatus of claim 10 wherein said conductive surface comprises a stainless steel or aluminum roller.

12. The apparatus of claim 11 wherein said conductive roller includes a conductive polymer coating on the surface thereof.

13. The apparatus of claim 10 wherein said means for measuring electrical resistance further comprises means for varying its sensitivity.

14. The apparatus of claim 13 wherein said means for varying of sensitivity comprises means for varying said voltage applied to said circuit.

15. The apparatus of claim 14 wherein said means for varying of sensitivity further comprises means for timing a length of reduced electrical resistance in said circuit.

16. The apparatus of claim 13 wherein said means for varying of sensitivity comprises means for timing a length of reduced electrical resistance in said circuit.

17. The apparatus of claim 10 further comprising means for activating an alarm in response to a determination of a coating discontinuity.

18. The apparatus of claim 10 further comprising means for ceasing coating of said nonconductive material onto said conductive material web in response to a determination of a coating discontinuity.

19. The apparatus of claim 10 further comprising means for marking said web in response to a determination of a coating discontinuity.

20. The apparatus of claim 19 wherein said marking means comprises an ink jet marker.

21. The apparatus of claim 19 wherein said marking means comprises a tape marker.

22. The apparatus of claim 10 wherein said masking means comprises a non-conductive tape.

23. The apparatus of claim 10 wherein said masking means comprises a plastic collar.

* * * * *